US012721573B2

(12) United States Patent
Schipper et al.

(10) Patent No.: US 12,721,573 B2
(45) Date of Patent: Sep. 1, 2026

(54) METHOD, COMPUTER PROGRAM PRODUCT, COMPUTER-READABLE STORAGE MEDIUM AND SYSTEM

(71) Applicant: KONINKLIJKE PHILIPS N.V., Eindhoven (NL)

(72) Inventors: Alphonsus Tarcisius Jozef Maria Schipper, Stramproy (NL); Pedro Miguel Ferreira Dos Santos Da Fonseca, Borgerhout (BE); Ruud Johannes Gerardus Van Sloun, Eindhoven (NL); Sebastiaan Overeem, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 147 days.

(21) Appl. No.: 18/610,332

(22) Filed: Mar. 20, 2024

(65) Prior Publication Data

US 2024/0315645 A1 Sep. 26, 2024

(30) Foreign Application Priority Data

Mar. 24, 2023 (EP) .................................... 23164059

(51) Int. Cl.
*A61B 5/00* (2006.01)
*A61B 5/0205* (2006.01)
(Continued)

(52) U.S. Cl.
CPC .............. *A61B 5/72* (2013.01); *A61B 5/0205* (2013.01); *A61B 5/352* (2021.01); *A61B 5/4812* (2013.01);
(Continued)

(58) Field of Classification Search
CPC ......... A61B 5/72; A61B 5/352; A61B 5/0205; A61B 5/4812; A61B 5/4818;
(Continued)

(56) References Cited

U.S. PATENT DOCUMENTS

2002/0128564 A1* 9/2002 Carlson .............. A61B 5/02405 600/509
2003/0078624 A1* 4/2003 Carlson .............. A61N 1/36542 607/9

(Continued)

OTHER PUBLICATIONS

Sprager et al., "Optimization of Heartbeat Detection in Fiber-Optic Unobtrusive Measurements by Using Maximum A Posteriori Probability Estimation", IEEE Journal of Biomedical and Health Informatics, vol. 18, No. 4, Jul. 2014, pp. 1161-1168.

(Continued)

*Primary Examiner* — Michael Tomaszewski
(74) *Attorney, Agent, or Firm* — Michael W. Haas

(57) ABSTRACT

There is provided a method to estimate a period characteristic, such as period length or a period location, of a physiological rhythm, such as a cardiac rhythm or a spontaneous breathing rhythm. The method comprises receiving the signal representing the physiological rhythm, estimating a first group of period characteristic estimations based on the signal, generating a prior probability for the period characteristic based on at least a subset of the first group of period characteristic estimations, and estimating a second group of period characteristic estimations based on the first group and the prior probability. By using this method, the accuracy of the signal is improved, especially when the signal is obtained from an accelerometer arranged on the chest of the subject.

11 Claims, 9 Drawing Sheets

(51) Int. Cl.

| | |
|---|---|
| ***A61B 5/352*** | (2021.01) |
| *A61B 5/024* | (2006.01) |
| *A61B 5/113* | (2006.01) |

(52) U.S. Cl.

CPC .......... *A61B 5/4818* (2013.01); *A61B 5/6823* (2013.01); *A61B 5/02405* (2013.01); *A61B 5/113* (2013.01); *A61B 5/6831* (2013.01); *A61B 2505/07* (2013.01); *A61B 2562/0219* (2013.01)

(58) Field of Classification Search

CPC ... A61B 5/6823; A61B 5/02405; A61B 5/113; A61B 5/6831; A61B 2505/07; A61B 2562/0219

USPC .......................................................... 600/301

See application file for complete search history.

(56) References Cited

U.S. PATENT DOCUMENTS

| | | | | |
|---|---|---|---|---|
| 2004/0230105 | A1* | 11/2004 | Geva | A61B 5/7275 600/509 |
| 2007/0129641 | A1* | 6/2007 | Sweeney | A61N 1/36542 600/513 |
| 2015/0157269 | A1* | 6/2015 | Lisogurski | A61B 5/6838 600/301 |
| 2015/0220486 | A1* | 8/2015 | Karakonstantis | G06F 17/142 708/405 |
| 2016/0007870 | A1* | 1/2016 | Brueser | A61B 5/6892 600/509 |
| 2016/0022166 | A1* | 1/2016 | Stadler | A61B 5/1116 600/483 |
| 2016/0171170 | A1* | 6/2016 | Clifton | A61B 5/7267 703/2 |
| 2017/0017769 | A1* | 1/2017 | Tekumalla | A61B 5/7267 |
| 2018/0177425 | A1* | 6/2018 | Stadler | A61N 1/3627 |
| 2018/0185660 | A1* | 7/2018 | Eddy | A61N 1/3704 |
| 2020/0121207 | A1* | 4/2020 | Brüser | A61B 5/6892 |
| 2021/0093215 | A1* | 4/2021 | Hopper | A61B 5/0031 |
| 2022/0062646 | A1* | 3/2022 | Galarneau | A61N 1/3714 |
| 2022/0168575 | A1* | 6/2022 | Greenhut | A61N 1/36578 |
| 2023/0041884 | A1* | 2/2023 | Mohiuddin | G16H 10/60 |
| 2024/0315645 | A1* | 9/2024 | Schipper | A61B 5/0816 |

OTHER PUBLICATIONS

Tobar et al., "Bayesian Reconstruction of Fourier Paris", IEEE Transactions on Signal Processing, vol. 69, 2021, pp. 73-87.

Paalasmaa et al., "A respiratory latent variable model for mechanically measured heartbeats", IOP Publishing, Physiological Measurement 31, (2010), pp. 1331-1344.

Bakker et al., "Estimating sleep stages using cardiorespiratory signals: validation of a novel algorithm across a wide range of sleep-disordered breathing severity Journal of Clinical Sleep Medicine" Journal of Clinical Sleep Medicine, vol. 17, Issue 7, pp. 1343-1354, Jul. 1, 2021.

Bonomi et al., "Atrial Fibrillation Detection Using a Novel Cardiac Ambulatory Monitor Based on Photo-Plethysmography at the Wrist", Journal of the American Heart Association, vol. 7, Issue 15, Aug. 7, 2018.

Cocconcelli et al., "High-Accuracy, Unsupervised Annotation of Seismocardiogram Traces for Heart Rate Monitoring", IEEE Transactions on Instrumentation and Measurement, vol. 69, No. 9, Sep. 2020, pp. 6372-6380.

D'Mello et al., Autocorrelated Differential Algorithm for Real-Time Seismocardiography Analysis IEEE Sensors Journal, vol. 19 Issue 13, Jul. 1, 2019, pp. 5127-5140.

Dubey et al., "Harmonic sum-based method for heart rate estimation using PPG signals affected with motion artifacts", Journal of Ambient Intelligence and Humanized Computing, 9(1), Oct. 15, 2016, pp. 137-150.

Gardner et al., "A Wearable Ballistocardiography Device for Estimating Heart Rate During Positive Airway Pressure Therapy: Investigational Study Among the General Population", JMIR Cardio 2021, vol. 5, Iss. 1, e26259, pp. 1-13.

Kathirvel et al., An Efficient R-peak Detection Based on New Nonlinear Transformation and First-Order Gaussian Differentiator, Cardiovascular Engineering and Technology, vol. 2, No. 4, Dec. 2011, pp. 408-425.

Mallinson, "A survey into paramedic accuracy in identifying the correct anatomic locations for cardiac auscultation" British Paramedic Journal, vol. 2 Issue 2, 2017, pp. 13-17.

Rai et al., "A Comprehensive Review on Seismocardiogram: Current Advancements on Acquisition, Annotation, and Applications" Mathematics, vol. 9 Issue 18, 2243, pp. 1-28, 2021.

Schipper et al., "Estimation of respiratory rate and effort from a chest-worn accelerometer using constrained and recursive principal component analysis", IOPScience, Physiological Measurement, 42, (2021), 045004, pp. 1-15.

Shaffer et al., (2017) "An Overview of Heart Rate Variability Metrics and Norms", Frontiers in Public Health, vol. 5, Article 258, pp. 1-17, Sep. 28, 2017.

Wahlstroem et al., "A Hidden Markov Model for Seismocardiography", IEEE Transactions on Biomedical Engineering, vol. 64, No. 10, Oct. 2017, pp. 2361-2372.

"Part 7.3: Management of Symptomatic Bradycardia and Tachycardia" (2005) Circulation, 112(24_supplement), p. pp. IV-67-IV-77. Available at: https://doi.org/10.1161/CIRCULATIONAHA. 105. 166558.

Brueser et al., "Robust inter-beat interval estimation in cardiac vibration signals", Physiological Measurement, 34(2), pp. 123-138. (2013).

Van Gilst et al. "Protocol of the SOMNIA project: an observational study to create a neurophysiological database for advanced clinical sleep monitoring", BMJ Open, 9(11), p. e030996-1-9, (2019).

"Heart Rate Variability", European Heart Journal, vol. 17, (Mar. 1996), American Heart Association Inc, European Society of Cardiology, 17, pp. 354-381.

* cited by examiner

METHOD, COMPUTER PROGRAM PRODUCT, COMPUTER-READABLE STORAGE MEDIUM AND SYSTEM

CROSS REFERENCE TO RELATED APPLICATION

This application claims the benefit of European Patent Application Serial No. 23164059.0, filed Mar. 24, 2023. This application is incorporated by reference herein.

FIELD OF THE INVENTION

The invention relates to a method of processing a signal representing a physiological rhythm of a subject. The physiological rhythm has a period characteristic. The invention further relates to a computer program product and a computer-readable storage medium, each having instructions which, when executed by a computer, cause the computer to carry out the method. Further, the invention relates to a system for processing a signal representing a physiological rhythm of a subject.

BACKGROUND OF THE INVENTION

Accurate knowledge of physiological rhythms, such as heart rate or respiratory rate, is of crucial importance in many healthcare applications including diagnosis, patient monitoring, and treatment. Accordingly, the estimation of the time-varying frequencies of these rhythms from conventional clinical measurement modalities such as electrocardiogram (ECG), pulse oximetry, or respiratory inductance plethysmography is a well-studied problem. While for some applications, it might be sufficient to estimate only an average frequency over multiple periods of the underlying rhythm, others such as heart rate variability (HRV) analysis require an event-to-event resolution.

Due to demographic changes and the growing numbers of patients with chronic conditions, home monitoring of a patient's health status will play an important role in future healthcare systems. Recent studies have shown that home telehealth approaches can lead to a significant reduction of hospital admissions and numbers of bed days of care.

Since conventional measurement modalities are rarely applicable outside of clinical settings, unobtrusive and unconstrained measurement systems are currently emerging as a way to allow continuous long-term monitoring of a patient's health status. These systems aim to provide two advantages over current approaches in that they usually require no user interaction or compliance to perform their measurements and they do not interfere with the user's daily routine. Unobtrusive measurement systems based on a variety of different principles are known. These include capacitively coupled electrodes for ECG measurements in a chair or a car seat, capacitive respiration measurement in bed, radar, millimeter-wave interferometry, and ballistocardiography (BCG) or seismocardiography (SCG) sensors integrated into beds, chairs and weighing scales. Other types of unobtrusive measurement system include wearable systems. These measurement systems are implemented, for example, as wristwatches, pendants, and chestbands.

While these measurement systems offer the aforementioned advantages over established methods, they also come with their own set of drawbacks. Most notably, the signal quality can be highly varying and unreliable due to the often uncontrolled environment in which the measurements are performed. For some types of sensors, the morphology of the recorded signals can change drastically depending on the orientation and position of the user with respect to the sensor. This can be observed, for instance, in the case of bed-mounted BCG sensors which record cardiac vibrations caused by the contraction of the hearts and the ejection of blood into the aorta. In case of a wearable measurement system, the signal changes drastically in response to a change of posture of the patient.

Under these circumstances, reliable estimation of instantaneous frequencies (or their inverse: local interval lengths) can pose a significant challenge to algorithms which were originally developed for clinical use. These algorithms are often based on detecting a particular feature of the signal relating to the event of interest, such as the QRS complex in the ECG. Instantaneous frequencies are then computed by differencing successive occurrence times of these events. In the case of the ECG, sophisticated methods have been proposed to improve the robustness of the instantaneous heart rate estimation. However, these methods are usually limited to one type of signal and require extensive prior knowledge about the expected morphology of the waveform. As mentioned above, these requirements do not hold for unobtrusive sensors types.

SUMMARY OF THE INVENTION

It is an objective of the invention to provide an improved method to process a signal representing a physiological rhythm of a subject. Optionally, the objective of the invention is to provide a method to obtain improved information representing the physiological rhythm for different postures of the subject.

According to a first specific aspect, there is provided a method of processing a signal representing a physiological rhythm of a subject, the physiological rhythm having period characteristic, the method comprising:

- receiving the signal;
- estimating a first group of period characteristic estimations based on the signal;
- generating a prior probability for the period characteristic based on at least a subset of the first group of period characteristic estimations;
- estimating a second group of period characteristic estimations based on the first group and the prior probability.

Based on the signal, the first group of period characteristic estimations is estimated. The first group comprises estimations for the period characteristic for a plurality of periods of the physiological rhythm. In most cases, the first group of period characteristic estimations provides a good estimation of the period characteristic for some periods, whereas the first group provides a poor estimation of the period characteristic for other periods. The poor estimations are, for example, the result of a movement of the subject, or any other type of event that negatively affects the signal from accurately representing the physiological rhythm.

Based on the first group of period characteristic estimations, a prior probability is generated. The prior probability distinguishes between probable and improbable estimations of the period characteristic, based on the information from the first group of period characteristic estimations. The prior probability is based on the whole first group or based on a subset of the first group. For example, the subset comprises fewer poor estimations of the period characteristic that the first group. For example, the subset group contains only good estimations of the period characteristic. Physiological rhythms have some predictable properties. For example, the upper limit and the lower limit of a heart rate of a subject is known, as well as that the heart rate can only gradually change over time. In another example, the upper limit and the lower limit of a spontaneous breathing rhythm of a subject is known. For example, estimations from the first group that exceed such limits are excluded from the subset.

By estimating the second group of period characteristic estimations based on the first group and the prior probability, the period characteristic of the physiological rhythm is estimated more accurately. Especially for the parts of the signal for which the first group initially provided a poor estimation, the accuracy is improved. As a result, a more accurate estimation of the period characteristic of the physiological rhythm is provided, even in case the subject moves or changes posture. This way, accurate estimations of the physiological rhythm can be obtained even with unobtrusive and unconstrained measurement systems. Optionally, the period characteristic of the physiological rhythm is estimated more accurately for the parts of the signal, for which first group initially provided already a good estimation. This way, an improved accuracy of the period characteristic estimation is obtained.

Physiological rhythms, such as heartbeats and the spontaneous breathing rhythm, have a repetitive nature. A repetition in the physiological rhythm is characterized by a period. The period is defined as the time between two repetitions. For example, the period is the time between two events in the physiological rhythm. For example, the period is the time between two heart beats, or the time between starting two consecutive inhales. A period has at least one period characteristic, such as a period length, or a frequency of the rhythm, or a timing of a phase in the period, such as the start or the end of the period. For example, the period characteristic is a physiological event that occurs every period under normal circumstances. Examples of such physiological events are the opening of the atrioventricular valves, or reversing the airflow from inhaling to exhaling. It is possible that such a physiological event does not occur every period due to an illness or a condition of the subject.

The signal comprises information about the physiological rhythm. The signal is, for example, generated by a measurement device configured to generate the signal in response to measuring a physiological property of a subject. The measurement device is, for example, configured to measure a heartbeat, or a pulse or respiratory movement or an airflow caused by breathing. For example, the signal is an electric signal. For example, the signal comprises signals from multiple sensors. For example, the multiple sensors measure the physiological rhythm of the subject simultaneously.

Based on the signal, the method estimates the first group of period characteristic estimations, for example by determining a local periodicity spectrum.

Due to the predictable nature of physiological rhythms, a prior probability is generated based on the first group of period characteristic estimations. A prior probability is alternatively known as a prior probability distribution or simply as prior. A prior probability uses statistics to give a probability of the values of the period characteristic estimations in the first group.

The prior probability uses, for example, additional information. For example, the additional information comprises information about the limits of the physiological rhythm of the subject, such as a maximum heartrate. For example, the additional information comprises information about the activity that the subject is doing while the signal is being generated. For example, such an activity is sleeping or sitting or lying or walking etc.

The prior probability uses, for example, only a subset of the first group of period characteristic estimations. Due to various reasons, part of the signal may not give a good representation of the physiological rhythm. For example, during the time that part of the signal was obtained, the measuring device was not well placed, or the subject was moving excessively. The first group of period characteristic estimations may give very unrealistic estimations based on that part of the signal. By excluding those unrealistic estimations, the prior probability is improved.

The second group of period characteristic estimations is estimated based on the first group and the prior probability. By using the prior probability, the probability of a value of the period characteristic estimation of the first group for a certain period is evaluated. In case the prior probability indicates that the probability of the value is high, the period characteristic estimation is an accurate estimation. In case the prior probability indicates that the probability of the value is low, the period characteristic estimation is an inaccurate estimation. In that case, the period characteristic estimation is re-estimated using the value from the first group and the prior probability. The second group of period characteristic estimations comprises, for example, some values of the period characteristic estimations from the first group and some re-estimated values of the period characteristic estimations based on the values of the first group and the prior probability.

In an example, the second group of period characteristic estimations are not based on the complete first group, but only on a portion of the first group. For example, the second group is based on the portion of the first group that provides at least a minimum level of accuracy. For example, the second group is not based on a portion of the first group which has very bad estimations of the period characteristics. The very bad estimations may be the result of a significant error in the measurement that generated the signal. When the signal suffers from such a significant error, the signal does not contain realistic information representing the physiological rhythm, and is therefore not processed any further.

The method comprises determining a spectral likelihood of at least part of the signal. The spectral likelihood is representative of a likelihood that the first group of period characteristic estimations corresponding to the at least part of the signal represents the period characteristic of the physiological rhythm. The method further comprises estimating the second group of period characteristic estimations is based on the spectral likelihood of the signal.

The spectral likelihood transforms the signal from the time-domain to a frequency-domain. The spectral likelihood represents the signal as a series of periodicities. The spectral likelihood compares the similarity of one periodicity of the signal with another periodicity of the signal. For example, the spectral likelihood compares two adjacent periodicities of the signal. The spectral likelihood indicates the likelihood of a value for a period length of a period in the signal. For example, the spectral likelihood indicates the most likely value for a period length of a period in the signal. By taking the likelihood of the values for the period lengths of the periods in the signal into account, the estimations of the period characteristics are estimated more accurately.

The method comprises defining a localization point in the physiological rhythm. The localization point characterizes a phase in a period of the physiological rhythm. The method comprises determining a temporal likelihood of the signal corresponding to the period. The temporal likelihood is representative of a likelihood that the signal represents the localization point. The method comprises estimating the localization point based on the spectral likelihood, the temporal likelihood, and the prior probability.

To define a timing of a period of the physiological rhythm, a localization point is defined. The localization point characterizes a phase in the period of the physiological rhythm. For example, the localization point indicates a start of the period or an end of the period. For example, the localization point indicates a periodical event in the physiological rhythm that results in a prominent feature in the signal. The prominent feature is, for example, a large positive value of the signal or a large negative value of the signal. The prominent feature is, for example, a maximum gradient in the signal or a zero gradient in the signal. In case the physiological rhythm is a cardiac rhythm, the phase in the period of the physiological rhythm is, for example, a heartbeat, or closing or opening of a heart value, such as the aortic value or the pulmonary value. The phase in the cardiac rhythm causes, for example, a large acceleration of the subject or a large electrical pulse, causing a prominent feature in the signal. In case the physiological rhythm is a spontaneous breathing rhythm, the phase in the period of the physiological rhythm is, for example, the start or the end of inhalation, the start of the end of exhalation, a pause between inhalation and exhalation, a pause between exhalation and inhalation, a change in direction of an airflow, or a pressure caused by the airflow from the subject. The phase in the spontaneous breathing rhythm causes, for example, a large acceleration of the subject or a maximum air pressure or a minimum pressure air, causing a prominent feature in the signal.

The temporal likelihood indicates the likelihood that a point in the signal in the time-domain represents the localization point. By estimating the localization point based on the spectral likelihood, the temporal likelihood, and the prior probability, the localization point is estimated accurately. This allows an accurate estimation of the timing of the phase of the physiological rhythm.

In an embodiment, the localization point of the physiological rhythm indicates one of i) the start of the period, ii) the end of the period, iii) the middle of the period.

In an embodiment, estimating the location point comprises using a maximum a-posteriori probability (MAP) estimation. The maximum a-posteriori probability (MAP) estimation is based on the spectral likelihood, the temporal likelihood, and the prior probability.

By using the MAP estimation to estimate the location point, the location point is estimated in a robust way, and provides the most probable value for the location point.

In an embodiment, the second group of period characteristic estimations estimates the period characteristic of the physiological rhythm with more accuracy than the first group of period characteristic estimations.

By estimating the period characteristic based on the first group and the prior probability, the period characteristic is estimated more accurately.

In an embodiment, the period characteristic comprises at least one of a period length and a time stamp.

The period length indicates the time between two successive periods. For example, the period length indicates the time between two heartbeats or the time between the start of two breathing cycles. The time stamp indicates the location of the period in time. The time stamp indicates when in time the period occurs, for example, when a characteristic point of the period occurs in time. The time stamp provides, for example, information about inter-beat intervals or heart rate variability.

In an embodiment, the physiological rhythm is a spontaneous breathing rhythm of the subject. For example, the period characteristic represents a breath frequency of the subject.

In an embodiment, the physiological rhythm is a cardiac rhythm of the subject. For example, the period characteristic represents a heartbeat frequency of the subject.

In an embodiment, the method comprises estimating at least one of an inter-beat interval and a heart rate variability of the cardiac rhythm based on the second group of period characteristic estimations.

Inter-beat intervals and heart rate variability are physiological parameters that provide valuable information about the physical condition of the subject. By accurately estimating one or both of these parameters, accurately information is obtained that may help a medical professional to assess the physical condition of the subject.

In an embodiment, the signal comprises a signal from an accelerometer arranged on the chest of the subject.

An accelerometer arranged on the chest of the subject is regarded by many people as a comfortable, unobtrusive and unconstrained way to obtain information about a physiological rhythm. The accelerometer is configured to generate the signal based on the physiological rhythm, such as the breathing rhythm or the cardiac rhythm. However, the signal of the accelerometer is also influenced by movement of the subject, or by the posture of the subject. Also, in case the subject moves, the accelerometer may displace relative to the subject, causing a change in the signal. Due to these influences, the signal from an accelerometer is less accurate than the signal of, for example, an ECG. However, by applying the method according to the invention to the signal of the accelerometer arranged on the chest of the subject, the accuracy of the signal is significantly improved. This provides accurate period characteristic estimations while using an easy-to-use measurement device, i.e., the accelerometer on the chest.

In an embodiment, the signal is representative of the physiological rhythm over a time period, wherein the subject is sleeping during the time period, for example sleeping in the range of 6-10 hours.

For example, the time period is more than 1 hour or more than 2 hours or more than 4 hours. For such long time periods, it is likely that the subject will move. The movement has a risk of deteriorating the accuracy of the signal. By applying the method according to the method, the signal can be obtained over a long time period, while providing the period characteristic estimations with an improved accuracy over that long time period. By obtaining information over the period characteristic over the long time period, more information about the physical condition of the subject is obtained.

In an embodiment, the method comprises determining an occurrence of a sleep disorder breathing (SDB) event based on the second group of period characteristic estimations.

A sleep disorder breathing (SDB) event is an event in which the breathing of the subject is disturbed during sleep. SDB's include apnea, such as obstructive sleep apnea (OSA) or central sleep apnea (CSA). During an SDB event, breathing is, for example, paused, blocked, or significantly reduced. An SDB event is, for example, hyponea. During an hyponea event, the airflow of the subject caused by breathing drops significantly, such as by at least 30%.

Due to the SDB event, the oxygen intake by the subject is reduced and/or the output of carbon dioxide by the subject is reduced. As a result of a SDB event, one or more physiological rhythms of the subject are affected. By using the method according to the invention to determine the occurrence of a SDB event, it is more accurately determined whether an SDB event occurred. This allows, for example, to the use of less accurate measuring devices, which are suitable for use at home, while still being able to determine the occurrence of SDB events with sufficient accuracy.

In an embodiment, the method comprises determining a sleep stage of the subject based on the second group of period characteristic estimations.

There are four sleep stages: Three non-rapid eye movement (NREM) sleep stages and one rapid eye movement (REM) sleep stage. The non-rapid eye movement (NREM) sleep stages are N1, N2 and N3. Sleep stages N1 and N2 are light sleep, whereas sleep stage N3 is deep sleep. The different sleep stages have some differences in the physiological rhythms of the subject. For example, the cardiac rhythm is slower during N3 than in N1 or N2. For example, the cardiac rhythm is more regular during N3 than during REM. For example breathing is more slowly during N2 and N3 than during N1. For example, breathing is less regular during REM than during N1-N3. Based on the period characteristic as estimated by the method according to the invention, the sleep stage of the subject is determined. For example, the duration and the frequency of each sleep stage is determined.

In an embodiment, the signal comprises a sum of three-dimensional acceleration data, wherein the sum of three-dimensional acceleration data is bandpass filtered, for example bandpass filtered with cutoff points of 3 and 25 Hz.

By using three-dimensional acceleration data, the signal is less affected by the posture of the subject or by the orientation of the measuring device relative to the subject. To make the signal more focused to accelerations caused by the physiological rhythm, the three-dimensional acceleration data is bandpass filtered. Accelerations below a certain cutoff point and accelerations above a certain cutoff point are not likely to be caused by the physiological rhythm, and are therefore filtered out of the three-dimensional acceleration data. For example, a bandpass filter with cutoff points of 3 and 25 Hz provides a good filtering. By using this bandpass filter, the three-dimensional acceleration data contains mostly or only data with a frequency between 3 and 25 Hz.

In an embodiment, the method comprises receiving information about the subject. Generating the prior probability is based on the information about the subject.

The prior probability is further improved by including information about the subject. This information is provided in addition to the first group of period characteristic estimations. The information includes, for example, the gender of the subject, the age, the weight or body mass index. The information includes, for example, information about a physical condition of the subject or about previous measurements of the physiological rhythm or about previous medical examinations.

In a second aspect of the invention, there is provided a computer program product, comprising instructions which, when executed by a computer, cause the computer to carry out the method of the first aspect of the invention.

In a third aspect of the invention, there is provided a computer-readable storage medium comprising instructions which, when executed by a computer, cause the computer to carry out the method of the first aspect of the invention.

In a fourth aspect of the invention, there is provided a system for processing a signal representing a physiological rhythm of a subject, the physiological rhythm having period characteristic, the system comprising a sensor and a computer, wherein the computer is coupled to the sensor, wherein the computer is configured to perform the method of the first aspect of the invention.

BRIEF DESCRIPTION OF THE DRAWINGS

Exemplary embodiments will now be described, by way of example only, with reference to the following figures, in which.

DETAILED DESCRIPTION OF EMBODIMENTS

Figure 1:
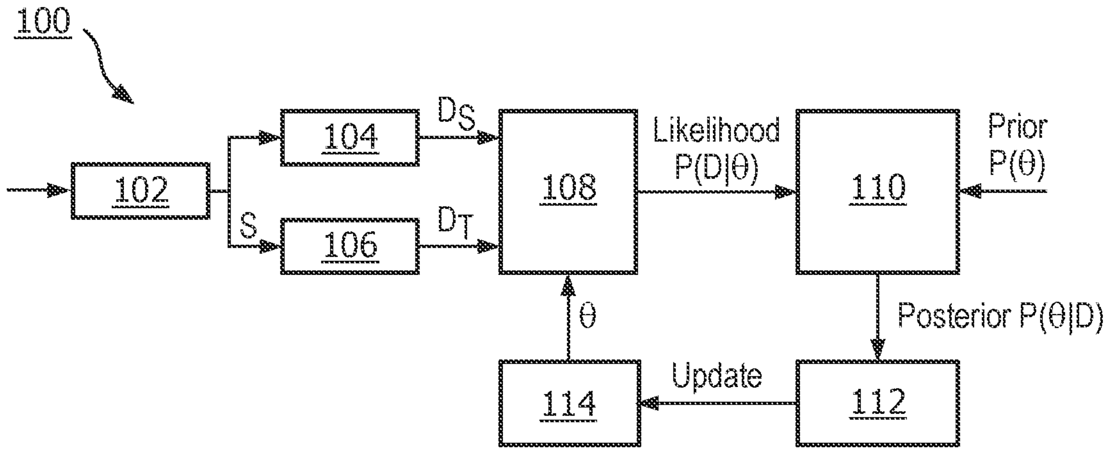
FIG. 1 depicts a first embodiment according to the invention.
Figure 10:
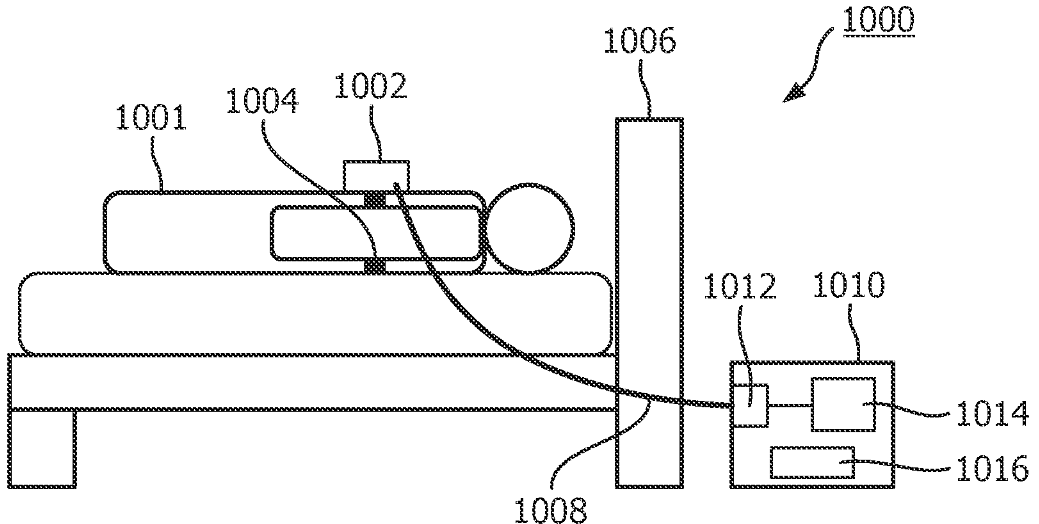
FIG. 10 depicts a system for processing a signal representing a physiological rhythm of a subject, according to a third embodiment of the invention.

FIG. 1 depicts an embodiment of the method according to the invention. In the method, a signal 100 representing a physiological rhythm of a subject 1001 is processed. The subject 1001 is depicted in FIG. 10. The physiological rhythm has a period characteristic. The method comprises receiving the signal 100; estimating a first group of period characteristic estimations based on the signal 100; generating a prior probability for the period characteristic based on at least a subset of the first group of period characteristic estimations; and estimating a second group of period characteristic estimations based on the first group and the prior probability.

In this embodiment, the physiological rhythm is a cardiac rhythm. The signal 100 is obtained with an accelerometer 1002 attached to the chest of the subject 1001, see FIG. 10. In an alternative embodiment, the physiological rhythm is a spontaneous breathing rhythm of the subject 1001.

The period characteristic comprises a period length and a time stamp.

The method makes use of a latent variable model 108. The latent variable model 108 is a statistical model that relates an observed variable to an (unobserved) latent variable. The latent variable θ is the period characteristic. The observed variable is the acceleration data D in the signal 100. To estimate the latent variable θ from the observed data D a maximum a posteriori estimation, or MAP estimation is used. The MAP estimation aims to find the most probable value of heartbeats θ given acceleration data D:

$$\theta_{MAP} = \text{argmax}_{\theta}\{P(\theta \mid D)\} \quad (1)$$

with P(θ|D) the posterior, being the probability of θ given D, which is computed using Bayes' rule:

$$P(\theta \mid D) = \frac{P(D \mid \theta)P(\theta)}{P(D)} \quad (2)$$

with P(D|θ) the likelihood, P(θ) the prior and P(D) the evidence. More information about these formulas is found in "A Student's Guide to Bayesian Statistics" by Lambert, B. (2018), Sage Publishing. The advantage of using the MAP estimation is that it allows for the use of a prior probability during estimation, such that it becomes possible to discourage improbable estimates, thereby making the method more robust.

The method as outlined in FIG. 1 has the following: the signal 100, a preprocessing step 102, a spectral transformation step 104, a temporal transformation step 106, the latent variable θ, a latent variable model 108, a prior probability P(θ), a computing step 110, a MAP searching step 112, an updating step 114 of the latent variable θ. More explanation about the various parts of the method as outlined in FIG. 1 is given below, with reference to other figures.

Figure 2:
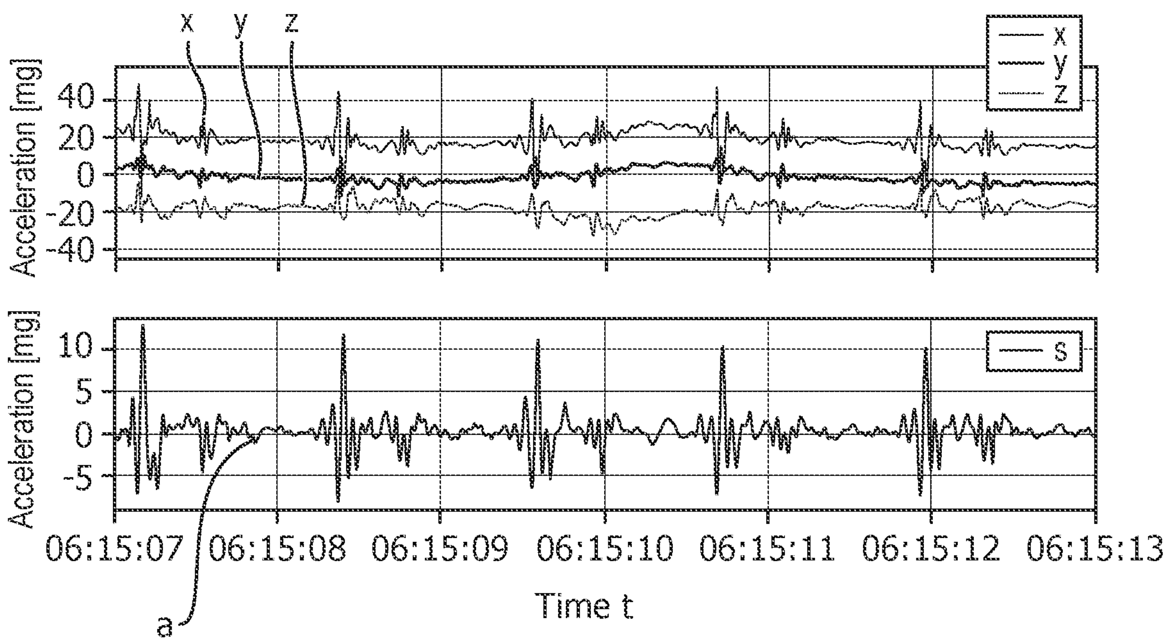
FIG. 2 depicts acceleration data in the signal according to the first embodiment.

FIG. 2 depicts the acceleration data D in the signal 100 according to the first embodiment as a function of time t. The acceleration data D shows a portion of the complete signal 100. The portion is about 6 seconds, from the time at 6 hours, 15 minutes and 7 second to 6 hours, 15 minutes and 13 seconds. The complete signal 100 is representative of the physiological rhythm over a time period, in which the subject 1001 is sleeping in the range of 6-10 hours.

After receiving the signal 100, the signal 100 is preprocessed in the preprocessing step 102. The signal 100 comprises raw three-dimensional acceleration data x,y and z. In the preprocessing step 102, the sum of the raw three-dimensional acceleration data is taken, such that a one-dimensional signal a is obtained:

$$a = x + y + z. \quad (3)$$

Subsequently, the one-dimensional signal a is bandpass filtered, to obtain the preprocessed signal s. The cut-off points of the bandpass filter are 3 and 25 Hz, and the sampling frequency of the one-dimensional signal a is 250 Hz.

Figure 3:
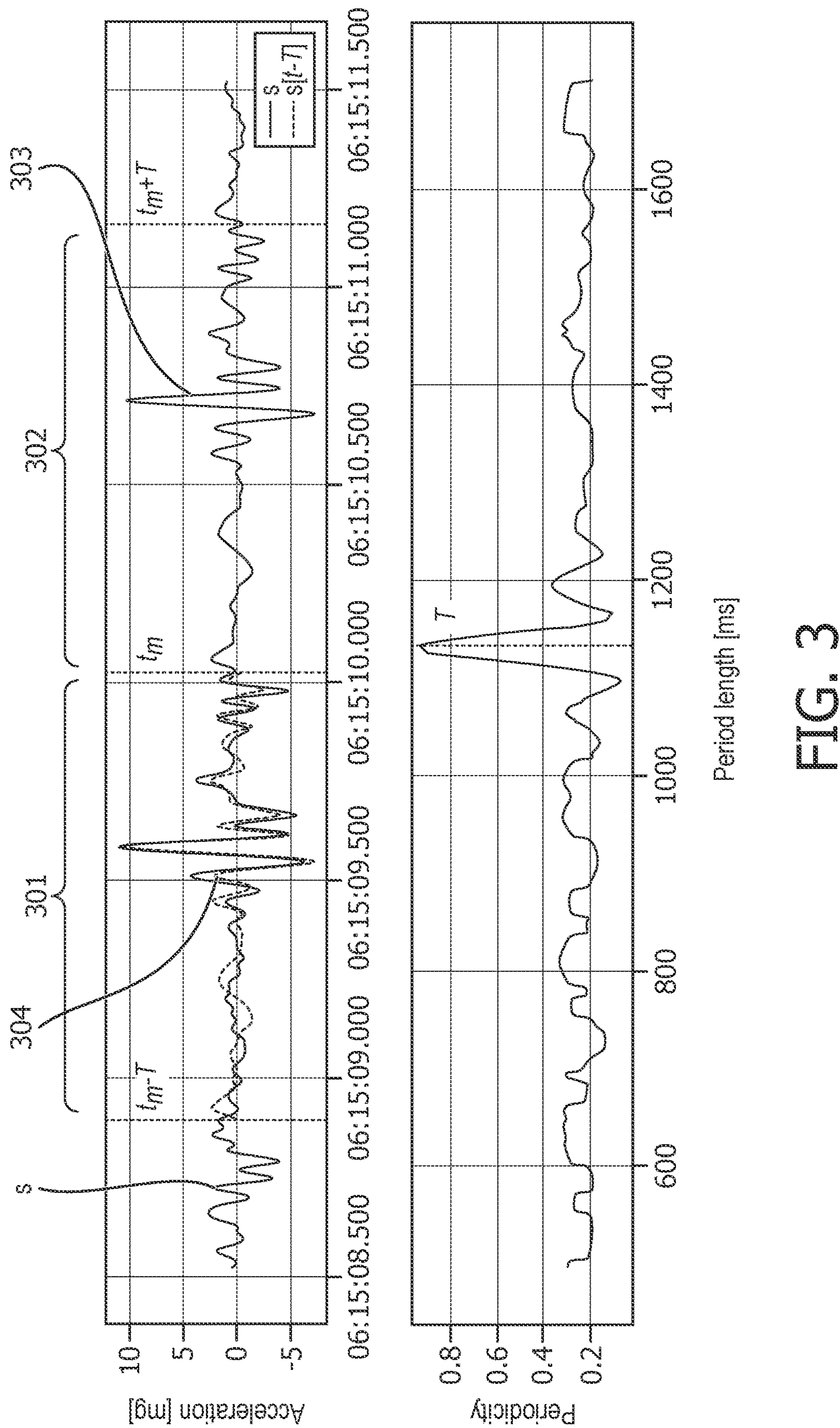
FIG. 3 depicts a chart representing shows the preprocessed signal according to the first embodiment.

FIG. 3 shows two periods 301, 302 of the preprocessed signal s. The estimation of the period characteristic of the two periods 301, 302 is estimated by centering the preprocessed signal s around $t_m$, and determine the periodicity spectrum as a function of T. T is the period length. A peak in the periodicity spectrum at T=1130 ms is found, which corresponds to maximum similarity between s[t-T] and s[t], as is shown by overlaying the signal 303 of preprocessed signal s in the period 302 in the period 301, which is shown as signal 304. This way, the period length T is estimated for the period 301. So in the period 301, the estimated period length in the first group is 1130 ms. This process is repeated for other periods in the preprocessed signal s. This results in the first group of period characteristic estimations based on the signal 100.

In the spectral transformation step 104, the preprocessed signal s is used to compute a local periodicity spectrum:

$$S_m(T) = p(s[t - T], s[t]) \quad (3)$$

with T the period length as estimated in FIG. 3, s the preprocessed signal, and p the periodicity function. The periodicity function p expresses the similarity between, s[t−T] and s[t], for $t_m<t<t_m+T$, with $t_m$ the center time of the spectrum. The periodicity function is based on modified versions of the autocorrelation, the average magnitude difference function (AMDF), and maximum amplitude pairs. Such calculation is known from 'Robust inter-beat interval estimation in cardiac vibration signals' by Brüser, C., Winter, S. and Leonhardt, S. (2013), Physiological Measurement, 34(2), pp. 123-138.

Figure 4:
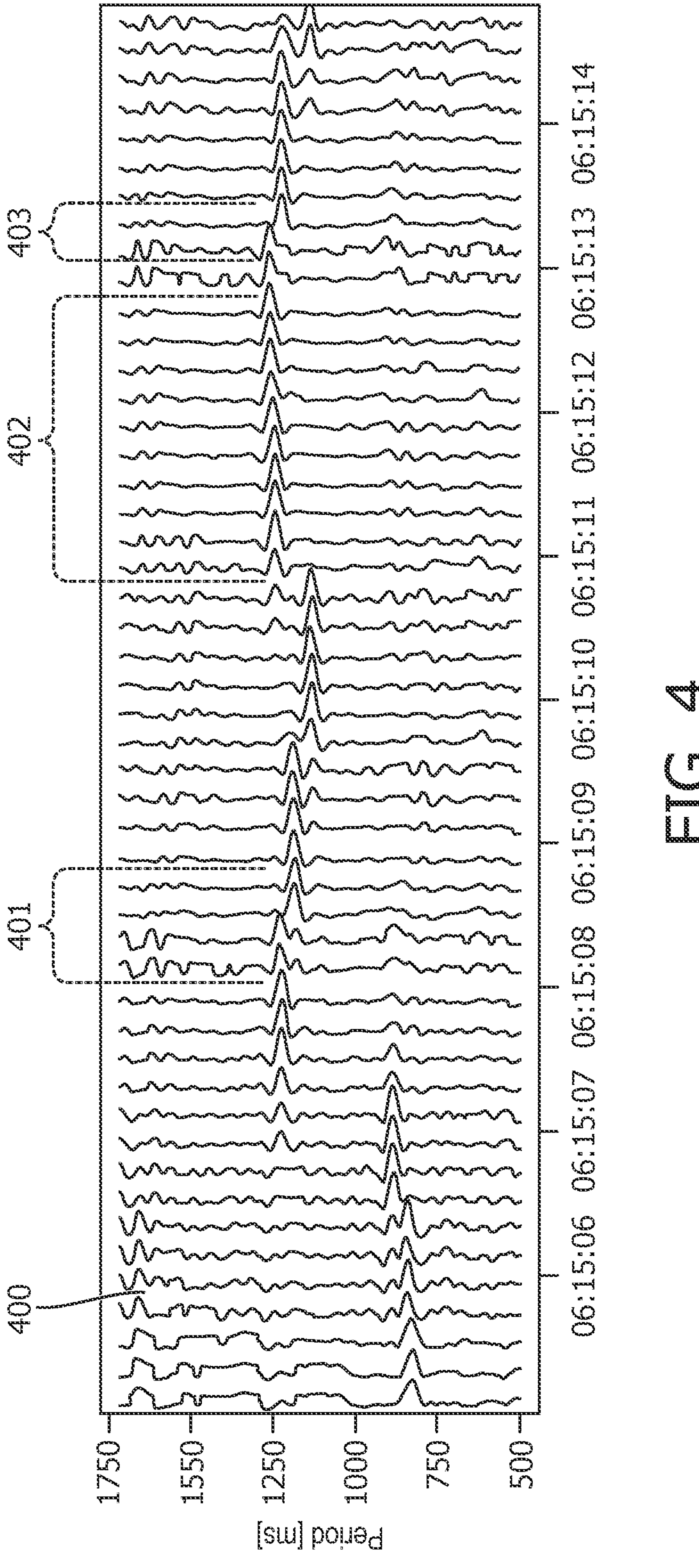
FIG. 4 depicts a spectrogram of periodicity according to the first embodiment.

The periodicity spectrum is computed every 200 ms, such that a spectrogram 400 of periodicity is obtained, which is depicted in FIG. 4. The spectrogram 400 depicts the estimated period length in [ms] as a function of time. The spectrogram 400 is relatively constant within an inter-beat interval and over inter-beat intervals that have the same length. Changes occur when the inter-beat interval changes, which coincides with the occurrence of a heartbeat. Around these changes, there is a gradual change of periodicity, which is visible as artifacts 401 and 403 in the spectrogram 400, at t=06:15:08 and at t=06:15:13 respectively. In contrast, at 402, which is around t=06:15:12, the spectrogram 400 is relatively constant over 2.5 s, while the inter-beat interval is 1250 ms. There is a heartbeat in the middle of that interval, and the inter-beat intervals before and after that beat are both 1250 ms long.

The spectral transformation step 104 improves accurately determining inter-beat intervals, which are period lengths T between successive heartbeats. To further improve the accuracy of the heartbeat timestamps, i.e., the beat localization, a temporal transformation step 106 is performed. The objective of the temporal transformation step 106 is to localize the heartbeats at a certain phase in the heart cycle. By using the certain phase for each period, the time difference between the time stamps correspond to the time differences between R-peaks in an ECG signal. In this embodiment, the points of maximum magnitude of acceleration data D in the preprocessed signal s are used.

The method comprises defining a localization point in the physiological rhythm, wherein the localization point characterizes the phase in a period of the physiological rhythm. The method comprises determining a temporal likelihood of the signal 100 corresponding to the period. The temporal likelihood is representative of a likelihood that the signal 100 represents the localization point. The method comprises estimating the localization point based on the spectral likelihood, the temporal likelihood, and the prior probability.

For example, the localization point of the physiological rhythm indicates the start of the period, the end of the period, or the middle of the period of the physiological rhythm.

The latent variable model 108 computes how well the data fits with the latent variable θ, in the form of a likelihood P(D|θ). The latent variable model 108 takes as input a value of the latent variable (the heartbeat timestamps and inter-beat intervals) and computes how well the spectrally and temporally transformed data fit with these timestamps and intervals, through the following relation:

$$P(D \mid \theta) = f(D, \theta) \cong f_T(D_T, \theta) f_S(D_S, \theta) \quad (4)$$

with f the likelihood function. $D_T$ the temporally transformed data, $D_S$ the spectrally transformed data, $f_T$ the temporal likelihood function, and $f_S$ the spectral likelihood function. The first equality states, without loss of generality, that the likelihood is a function of D and θ, while the second equality, which factorizes this function, is a modelling choice that we make.

The total spectral likelihood $f_{Stot}$ is then computed as follows:

$$f_{Stot}(D_S, \theta) = f_{Stot}(D_S, t, T) = f_{Stot}(D_S, t_1, t_2, \ldots, t_n, T_1, T_2, T_n) \cong \prod_i f_S(D_S, t_i, T_i) \quad (5)$$

in which the latter equality factorizes the likelihood into a product of functions ($f_S$), which is not unreasonable, as the spectrogram of periodicity ($D_S$) is only locally dependent on the occurrence of heartbeats. The likelihood of a heartbeat timestamp $t_i$ and associated inter-beat interval $T_i$ is then computed as follows:

$$f_S(D_S, t_i, T_i) = \left(\prod_m S_m(T_i)\right)^{1/p} \quad (6)$$

for all m with $t_i \le t_m \le t_i + T_i$, and p the number of spectra used. The computation comprises the multiplication of all spectra that have their center time $t_m$ within the inter-beat interval ($t_i$ $t_i+T_i$), such that (6) resembles a joint probability. The exponent 1/p is for the geometric mean, which prevents short inter-beat intervals (with smaller p) to be favored over longer inter-beat intervals (with larger p).

The method comprises determining a spectral likelihood of at least part of the signal 100. The spectral likelihood is representative of a likelihood that the first group of period characteristic estimations corresponding to the at least part of the signal 100 represents the period characteristic of the physiological rhythm. The method comprises estimating the second group of period characteristic estimations is based on the spectral likelihood of the signal 100. The second group of period characteristic estimations estimates the period characteristic of the physiological rhythm with more accuracy than the first group of period characteristic estimations.

Figure 5:
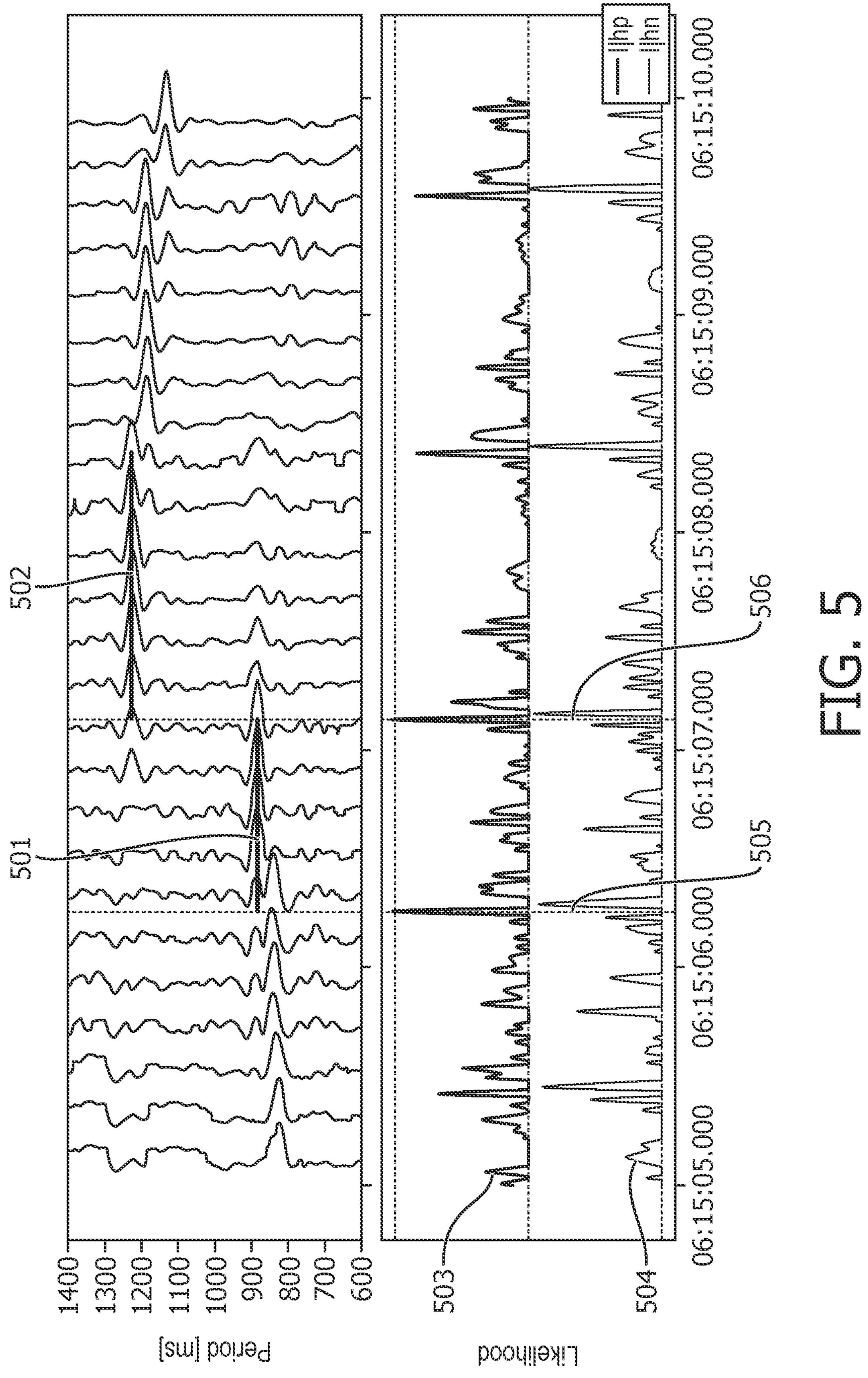
FIG. 5 depicts a spectral likelihood and a temporal likelihood according to the first embodiment.

FIG. 5 shows two inter-beat intervals 501 and 502 as horizontal lines in the top-part of the figure. The first interval 501 has a duration of 880 ms. The first interval 501 covers 4 vertical lines, i.e., 4 spectra (p=4), all having peaks at 880 ms. As a result, the spectral likelihood (6) is maximal at T=880 ms. The second interval 502 has a duration of 1225 ms. The second interval 502 covers 6 vertical lines, i.e., 6 spectra, all heaving have peaks at 1225 ms. As a result, the spectral likelihood is maximal as well at T=1225 ms.

For the total temporal likelihood frtot, a similar factorization as for the spectral likelihood is followed:

$$f_{Ttot}(D_T, \theta) = f_{Ttot}(D_T, t, T) = f_{Ttot}(D_T, t_1, t_2, \ldots, t_n) \cong \prod_i f_T(D_T, t_i) \quad (7)$$

in which the latter equality factorizes the likelihood into a product of functions $f_T$, which is equal to the value of the temporal likelihood at $t_i$:

$$f_T(D_T, t) = llh(t) \quad (8)$$

In FIG. 5, the bottom graph depicts the preprocessed signal s divided into two parts 503 and 504. Part 503 shows the positive values of the preprocessed signal s from FIG. 3. Part 504 shows the negative values of the preprocessed signal s from FIG. 3, but represented as positive values. FIG. 5 shows two successive heartbeat timestamps with vertical dashed lines 505 and 506. The likelihoods $llh(t_i)$ and $llh(t_i+T_i)$ are both located at maxima in the preprocessed signal s in part 503 at the lines 505 and 506 respectively. Because the spectral likelihood and temporal likelihood of the two heartbeats in FIG. 5 are at a maximum, the overall likelihood (6) is at a maximum as well.

The prior probability gives information on the probability of values of the latent variable θ, and helps prevent silly estimations, for example inter-beat intervals of 100 ms (corresponding to 600 bpm). The prior probability uses knowledge of the distribution of the latent variable θ over the measurement population. Next to knowing that the subject 1001 is human, the prior probability is made specific, for example by using the knowledge that the subject 1001 is lying down, such that shorter inter-beat intervals (due to higher heartrate) will be discouraged. Optionally, the prior probability takes into account probabilities of sequences, for example by using Markov models, or information from neural network models. For example, the prior probability is a personalized prior probability.

For example, the prior probability is a Gaussian prior $\mathcal{N}(\mu, \sigma)$, with $\mu=\mu(t)$. The value for σ is empirically set to twice the standard deviation of the difference between the input and output of median-filtered period lengths of the first group.

Figure 6:
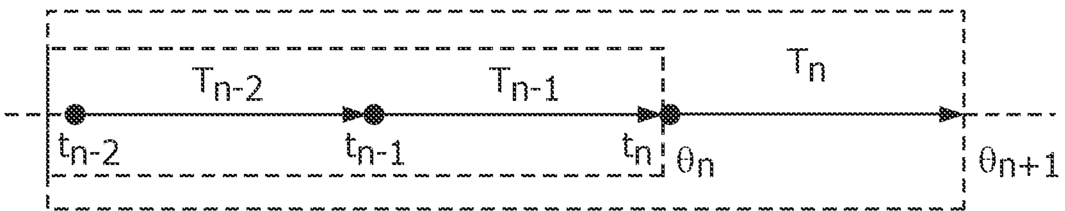
FIG. 6 depicts a representation of computing the posterior probability according to the first embodiment.

Based on the prior and the spectral likelihood and the temporal likelihood, the posterior probability is computed and maximized over the latent variable θ. To reduce the computational complexity of this problem, the approach is to break up the problem in smaller subproblems and to solve each of them recurrently. Assuming a partial solution $\theta_n$:

$$\theta_n = (t_n, T_{n-1}) = (t_1, \ldots, t_n, T_1, \ldots, T_{n-1}) \quad (9)$$

with $\theta_1=t_1$, see FIG. 6. Extending $\theta_n$ with one inter-beat interval and knowing the posterior probability of $\theta_n=P(\theta_n|D)$ then the posterior probability of the extended solution $\theta_{n+1}$ can be computed as follows:

$$P(\theta_{n+1} \mid D) = P(\theta_n, T_n \mid D) = P(T_n \mid D, \theta_n)P(\theta_n \mid D) \quad (10)$$

with the first equality using (9) and $t_{n+1}=t_n+T_n$, and the second following from $P(A,B)=P(A|B)\,P(B)$. Equation (10) is the basis of the MAP search engine as it is an expression for the posterior probability that is to be optimized using a MAP estimation. The right-hand side of (10) contains the posterior $P(T_n|D, \theta_n)$, which is computed in the computing step 110 using Bayes' rule:

$$P(T_n \mid D, \theta_n) = \frac{P(D \mid T_n, \theta_n)P(T_n \mid \theta_n)}{P(D)} \quad (11)$$

in which we discard P(D), as it is constant when maximizing the posterior, such that only the numerator remains. The numerator comprises the prior $P(T_n|\theta_n)$, which is computed based on the known distribution, and the likelihood P(|$T_n$, $\theta_n$), which is computed using the spectral likelihood and temporal likelihood functions from (6) and (7), to obtain:

$$P(D \mid T_n, \theta_n) = f_S(D_S, t_n, T_n) f_T(D_T, t_{n+1}). \tag{12}$$

Figure 7:
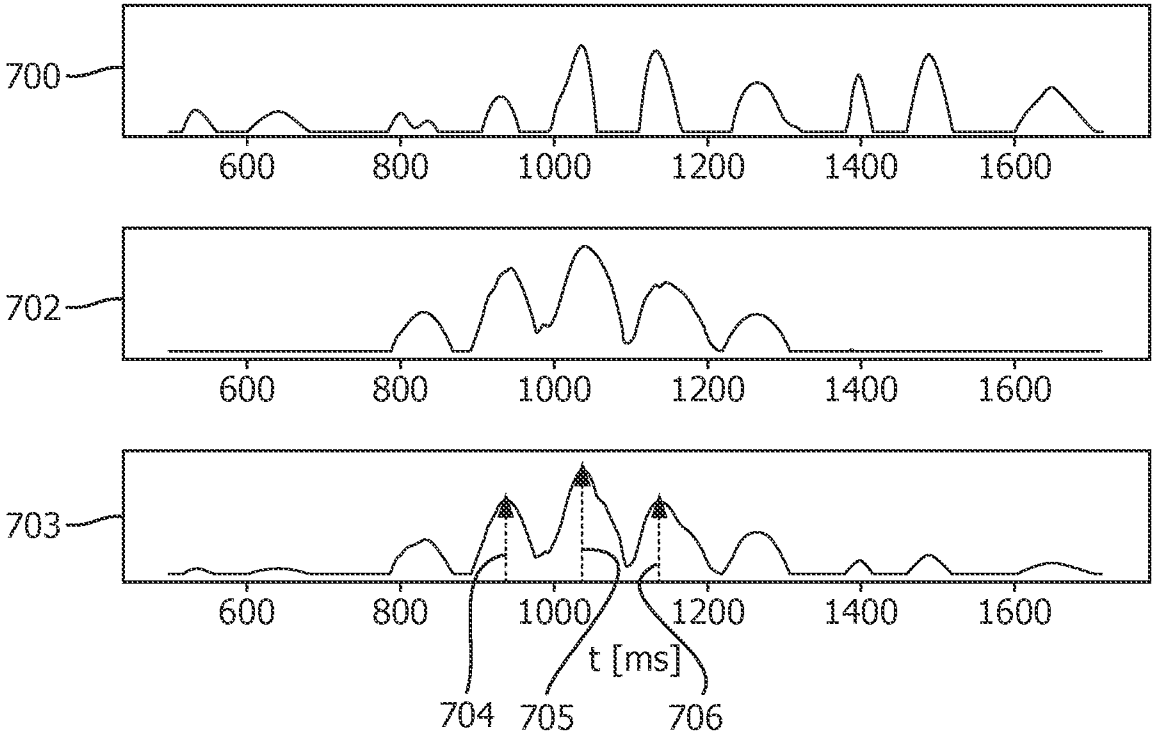
FIG. 7 depicts a representation of a computation of likelihoods and probabilities.

The computation of the numerator of (11) is outlined in FIG. 7, which shows likelihoods and probabilities in the log domain, such that the multiplications in (11) and (12) become additions, because if A=BC then log(A)=log(B)+log(C)). The top graph 700 of FIG. 7 shows the temporal log likelihood fr, the middle graph 702 shows the sum of the spectral log likelihood $f_S$ and the log prior P($T_n$|$\theta_n$), while the bottom graph 703 shows the log of the posterior P($T_n$|D, $\theta_n$).

The search space is discretized by not considering all values of $T_n$, when expanding a partial solution $\theta_n$, but only values of $T_n$ for which peaks exists in the posterior probability (13). This is outlined in FIG. 7. FIG. 7 shows the peaks with the arrows 704, 705, 706.

The recursive evaluation with constrained look-ahead starts at the start time $t_1$, which forms the first partial solution $\theta_1$. The posterior probability of $\theta_1$ is computed by:

$$P(\theta_1 \mid D) = f_T(D_T, t_1) \tag{13}$$

which is needed as initial value in equation (13). From the first partial solution, a tree search is performed, in which the branches are the peaks in the posterior (as in FIG. 7.), and the leaves are partial solutions $\theta_d$, with d the look-ahead depth. For example, d=8, to give a good balance between performance and computational load. During the recursive tree exploration, the posterior probability P($\theta_d$|D) was built up along the way, by recurrent application of (11). Then, the path with highest posterior probability was selected, and $\theta_1$ expanded, with the first inter-beat interval of the selected path, such that $\theta_2$ is obtained. This process is repeated until the partial solution covers all data and becomes a full solution.

Equation (11) defines the posterior probability P($T_n$|D, $\theta_n$) for a single inter-beat interval $T_n$. The approximation for the posterior probability, the numerator of (11), is then given as:

$$Q(T_n) = P(D \mid T_n, \theta_n) P(T_n \mid \theta_n) = f_S(D_S, t_n, T_n) f_T(D_T, t_{n+1}) P(T_n \mid \theta_n). \tag{14}$$

The method comprises estimating the time stamp using a maximum a-posteriori probability (MAP) estimation. The maximum a-posteriori probability (MAP) estimation is based on the spectral likelihood, the temporal likelihood, and the prior probability. The MAP estimation is computed in the MAP searching step 112.

The outcome of the MAP searching step 112 is used to update the latent variable θ in computing step 114.

Figure 8:
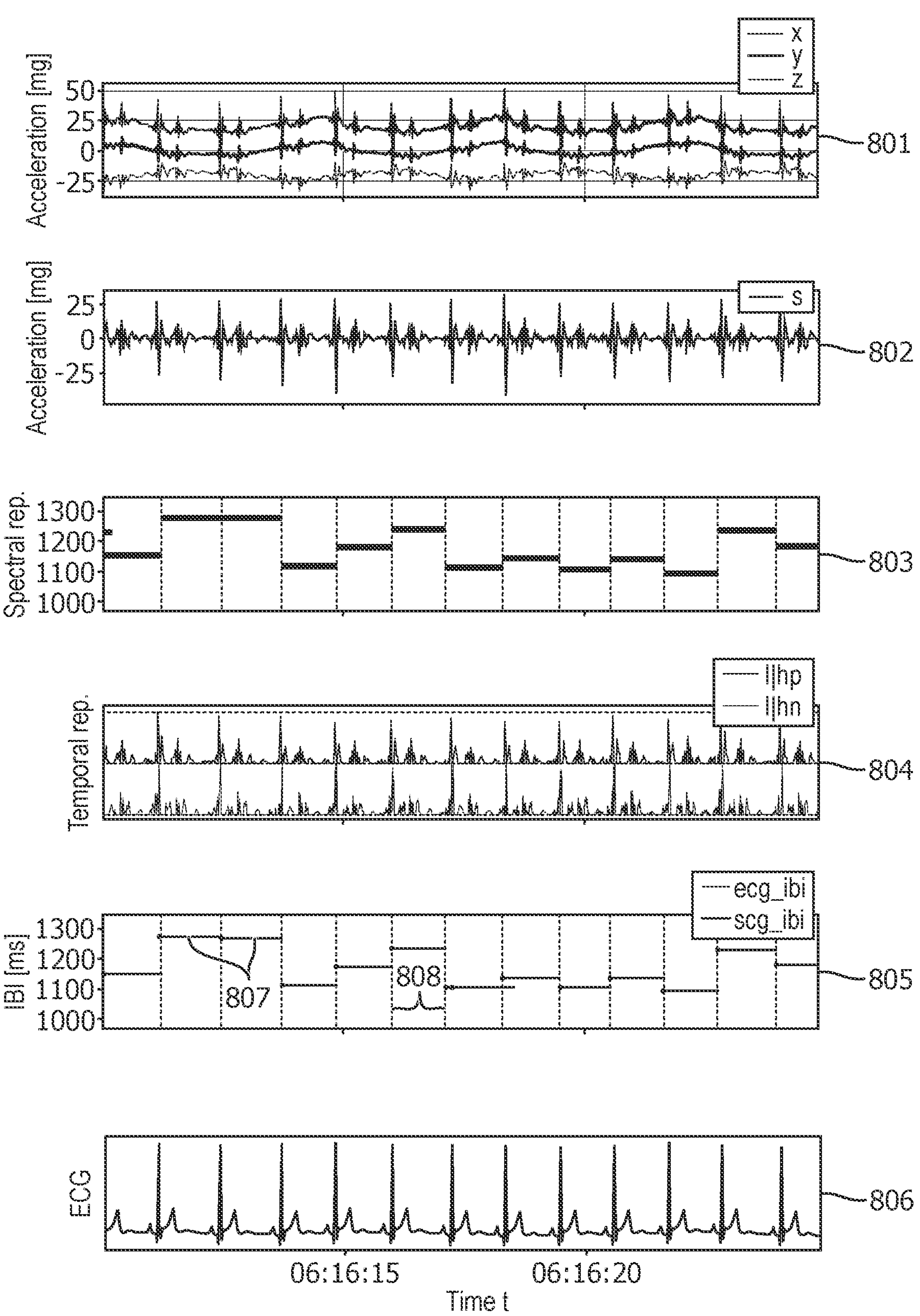
FIG. 8 shows various graphs representing steps according to the first embodiment.

FIG. 8 shows various graphs representing steps in the method according to the invention.

The graphs are at a function of time t.

The first graph 801 starts with the raw acceleration data D, x, y and z. The lines are plotted with adjusted offset for visibility. The peak-to-peak acceleration is approximately 50 mg.

The second graph 802 shows the one-dimensional signal after preprocessing. This is the preprocessed signal s.

The third graph 803 shows the spectral transformation of the preprocessed signal s.

The fourth graph 804 shows the temporal transformation of the preprocessed signal s.

The fifth graph 805 shows the result of the MAP estimation. The MAP estimation provides the most probable value of the latent variable θ, being the inter-beat intervals (IBI) in [ms] as horizontal lines 807, and heartbeat timestamps as dashed vertical lines 808. For clarity reasons, only two lines 807 and only two vertical lines 808 are numbered. The method allows the estimation of inter-beat intervals and heart rate variability of the cardiac rhythm based on the second group of period characteristic estimations.

The sixth graph 806 shows an ECG of the same cardiac rhythm as represented by the signal. The comparison between the fifth graph 805 and the sixth graph 806 shows that the inter-beat intervals and the heartbeats as estimated by the method according to the invention match accurately with the ECG.

In an embodiment, the method comprises determining an occurrence of a sleep disorder breathing (SDB) event based on the second group of period characteristic estimations. A SDB event is recognizable by a typical change in the cardiac rhythm.

In an embodiment, the method comprises determining a sleep stage of the subject 1001 based on the second group of period characteristic estimations.

Figure 9:
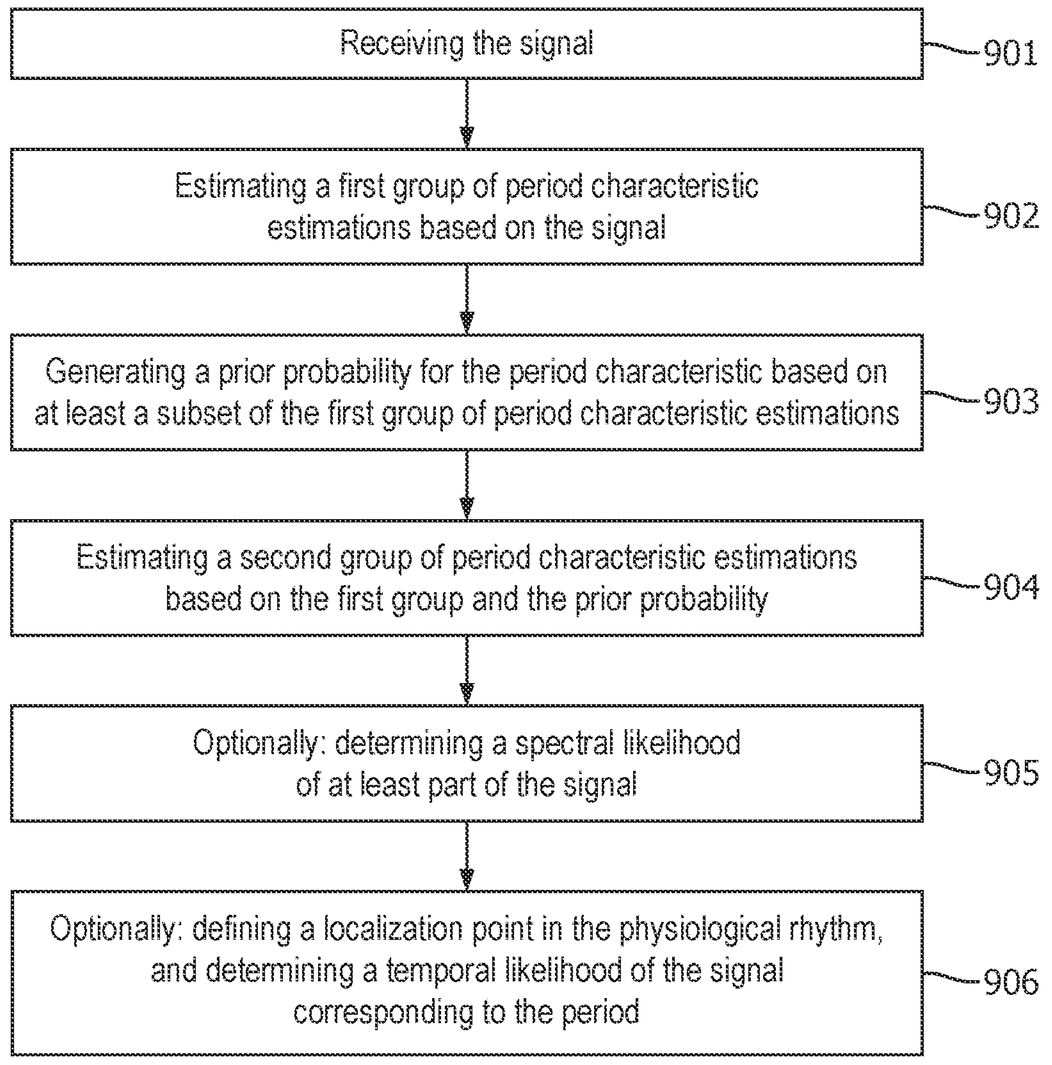
FIG. 9 depicts a method according to a second embodiment of the invention.

FIG. 9 depicts a method according to a second embodiment of the invention. The method is for processing the signal representing a physiological rhythm of a subject 1001. The physiological rhythm has a period characteristic. The method comprises receiving the signal 100 in step 901. The method comprises estimating a first group of period characteristic estimations based on the signal 100 in step 902. The method comprises generating a prior probability for the period characteristic based on at least a subset of the first group of period characteristic estimations in step 903. The method comprises estimating a second group of period characteristic estimations based on the first group and the prior probability in step 904.

In optional step 905, the method comprises determining a spectral likelihood of at least part of the signal 100. The spectral likelihood is representative of a likelihood that the first group of period characteristic estimations corresponding to the at least part of the signal 100 represents the period characteristic of the physiological rhythm. The method comprises estimating the second group of period characteristic estimations is based on the spectral likelihood of the signal 100.

In optional step 906, the method comprises defining a localization point in the physiological rhythm. The localization point characterizes a phase in a period of the physiological rhythm. The method comprises determining a temporal likelihood of the signal 100 corresponding to the period. The temporal likelihood is representative of a likelihood that the signal 100 represents the localization point. The method comprises estimating the localization point based on the spectral likelihood, the temporal likelihood, and the prior probability.

FIG. 10 depicts a system 1000 for processing a signal 100 representing a physiological rhythm of a subject 1001 1001.

The physiological rhythm has a period characteristic. The system 1000 comprising a sensor 1002 and a computer 1010. The computer 1010 is coupled to the sensor 1002 via a signal wire 1008. The computer 1010 is configured to perform the method of any one of the embodiments described above. The sensor 1002 is an accelerometer attached to the chest of the subject 1001 1001. The sensor 1002 is attached to the chest with a strap 1002. The subject 1001 1001 is lying on a bed 1006 and is asleep. The computer 1010 has an input device 1012 to connect to the sensor 1002 and to receive the signal 100 from the sensor 1002. The input device 1012 forwards the signal 100 to a processor 1014. The processor 1014 processes the signal 100 according to the method of any one of the embodiments described above. The processor 1014 is connected to an output device 1016. The output device 1016 outputs an output signal about the period characteristic as estimated by the method. For example, the output device 1016 generates a video signal or a Bluetooth signal or any other type of signal that is suitable to be used to convey information about the estimated period characteristic to a person.

The computer 1010 executes a computer program product, comprising instructions which, when executed by the computer 1010, cause the computer 1010 to carry out the method according to the invention. For example, the instructions are provided to the computer 1010 via a computer-readable storage medium comprising the instructions. For example, the computer 1010 has a memory to store the computer program product. The processor 1014 is configured to receive the instructions of the computer program product from the memory.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. The computer program product may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of processing a signal representing a physiological rhythm of a subject, the physiological rhythm having a period characteristic (T, ti), the method comprising:

receiving the signal from an accelerometer arranged on the subject, wherein the signal comprises raw three-dimensional acceleration data;

preprocessing the raw three-dimensional acceleration data by (a) summing axes to form a one-dimensional signal, and (b) bandpass filtering the one-dimensional signal;

estimating a first group of period characteristic (T, $t_i$) estimations based on the signal;

generating a prior probability (P(θ)) for the period characteristic (T, $t_i$) based on at least a subset of the first group of period characteristic (T, $t_i$) estimations;

estimating a second group of period characteristic (T, $t_i$) estimations based on the first group and the prior probability (P(θ));

determining a spectral likelihood ($f_S$) of at least part of the signal, wherein the spectral likelihood ($f_S$) is representative of a likelihood that the first group of period characteristic (T, $t_i$) estimations corresponding to the at least part of the signal represents the period characteristic (T, $t_i$) of the physiological rhythm, wherein estimating the second group of period characteristic (T, $t_i$) estimations is based on the spectral likelihood ($f_S$) of the signal;

defining a localization point in the physiological rhythm, wherein the localization point characterizes a phase in a period of the physiological rhythm;

determining a temporal likelihood ($f_T$) of the signal corresponding to the period, wherein the temporal likelihood ($f_T$) is representative of a likelihood that the signal represents the localization point; and estimating the localization point based on the spectral likelihood ($f_S$), the temporal likelihood ($f_T$), and the prior probability (P(θ)).

2. The method of claim 1, wherein estimating the location point comprises using a maximum a-posteriori probability (MAP) estimation, and wherein the maximum a-posteriori probability (MAP) estimation is based on the spectral likelihood ($f_S$), the temporal likelihood ($f_T$), and the prior probability (P(θ)).

3. The method of claim 1, wherein the second group of period characteristic (T, $t_i$) estimations estimates the period characteristic (T, $t_i$) of the physiological rhythm with more accuracy than the first group of period characteristic (T, $t_i$) estimations.

4. The method according to claim 1, wherein the period characteristic (T, $t_i$) comprises at least one of a period length (T) and a time stamp ($t_i$).

5. The method according to claim 1, wherein the physiological rhythm is a spontaneous breathing rhythm of the subject.

6. The method according to claim 1, wherein the physiological rhythm is a cardiac rhythm of the subject.

7. The method according to claim 6, comprising estimating at least one of an inter-beat interval and a heart rate variability of the cardiac rhythm based on the second group of period characteristic (T, $t_i$) estimations.

8. The method according to claim 5, wherein the signal comprises a signal from an accelerometer arranged on the chest of the subject.

9. The method according to claim 1, comprising: determining an occurrence of a sleep disorder breathing (SDB) event based on the second group of period characteristic (T, $t_i$) estimations.

10. The method according to claim 1, comprising: determining a sleep stage of the subject based on the second group of period characteristic (T, $t_i$) estimations.

11. A system for processing a signal representing a physiological rhythm of a subject, the physiological rhythm having a period characteristic (T, $t_i$), the system comprising:

a sensor disposed on the subject, where in the sensor is an accelerometer that generates the signal comprising raw three-dimensional acceleration data; and a computer, wherein the computer is in communication with the sensor, wherein the computer is configured to;

receive the raw three-dimensional acceleration data from the sensor;

preprocess the raw three-dimensional acceleration data by summing axes to form a one-dimensional signal and bandpass filtering the one-dimensional signal to define the signal;

estimate a first group of period characteristic $(T, t_i)$ estimations based on the signal;

generate a prior probability $(P(\theta))$ for the period characteristic $(T, t_i)$ based on at least a subset of the first group of period characteristic $(T, t_i)$ estimations;

estimate a second group of period characteristic $(T, t_i)$ estimations based on the first group and the prior probability $(P(\theta))$;

determine a spectral likelihood $(f_S)$ of at least part of the signal, wherein the spectral likelihood $(f_S)$ is representative of a likelihood that the first group of period characteristic $(T, t_i)$ estimations corresponding to the at least part of the signal represents the period characteristic $(T, t_i)$ of the physiological rhythm, wherein estimating the second group of period characteristic $(T, t_i)$ estimations is based on the spectral likelihood $(f_S)$ of the signal;

define a localization point in the physiological rhythm, wherein the localization point characterizes a phase in a period of the physiological rhythm;

determine a temporal likelihood $(f_T)$ of the signal corresponding to the period, wherein the temporal likelihood $(f_T)$ is representative of a likelihood that the signal represents the localization point; and estimate the localization point based on the spectral likelihood $(f_S)$, the temporal likelihood $(f_T)$, and the prior probability $(P(\theta))$.

* * * * *